United States Patent
Bergström et al.

(10) Patent No.: US 9,654,847 B2
(45) Date of Patent: May 16, 2017

(54) MONITORING AND DISPLAYING AN ABSORPTION STATE OF AN ABSORBENT ARTICLE

(71) Applicant: SCA Hygiene Products AB, Göteborg (SE)

(72) Inventors: Per Bergström, Göteborg (SE); Christer Olofsson Ranta, Västra Frölunda (SE); Björn Ålsnäs, Onsala (SE)

(73) Assignee: SCA HYGIENE PRODUCTS AB, Göteborg (SE)

( * ) Notice: Subject to any disclaimer, the term of this patent is extended or adjusted under 35 U.S.C. 154(b) by 0 days.

(21) Appl. No.: 14/787,514

(22) PCT Filed: Apr. 30, 2013

(86) PCT No.: PCT/EP2013/059045
§ 371 (c)(1),
(2) Date: Oct. 28, 2015

(87) PCT Pub. No.: WO2014/177203
PCT Pub. Date: Nov. 6, 2014

(65) Prior Publication Data
US 2016/0080841 A1    Mar. 17, 2016

(51) Int. Cl.
*G08C 19/22* (2006.01)
*H04Q 9/00* (2006.01)
*H04L 29/08* (2006.01)

(52) U.S. Cl.
CPC .............. *H04Q 9/00* (2013.01); *H04L 67/12* (2013.01)

(58) Field of Classification Search
CPC .... G01N 1/10; G01N 1/405; G01N 2030/009; G01N 2030/027; G01N 2030/085; G01N 30/06; H04L 67/12; H04Q 9/00
(Continued)

(56) References Cited

U.S. PATENT DOCUMENTS

| 7,250,547 B1 | 7/2007 | Hofmeister et al. |
| 7,977,529 B2 | 7/2011 | Bergman et al. |

(Continued)

FOREIGN PATENT DOCUMENTS

| EP | 2 527 823 | 11/2012 |
| JP | H05-245169 | 9/1993 |

(Continued)

OTHER PUBLICATIONS

English-language translation of a Japanese Office Action dated Oct. 31, 2016 issued in corresponding Japanese patent application No. 2016-510945.

*Primary Examiner* — Ojiako Nwugo
(74) *Attorney, Agent, or Firm* — Drinker Biddle & Reath LLP (57) ABSTRACT

A method of monitoring an absorption state of an absorbent article includes providing a logger unit, acquiring the absorption state of the absorbent article, and recording data indicating the acquired absorption state of the absorbent article in the logger unit. Acquiring the absorption state of the absorbent article and recording the data indicating the acquired absorption state of the absorbent article in the logger unit are each continuously performed during a monitoring period of the absorbent article. Also disclosed is a logger unit for performing this method; and a method of processing data indicating an absorption state of an absorbent article, which includes receiving sets of data indicating the absorption state of the absorbent article. Each of the sets of data indicates the absorption state of the absorbent article over a portion of a continuous period of time, and collating and/or displaying the data in continuous form. Also disclosed are data processing units for performing these data processing methods.

22 Claims, 7 Drawing Sheets

(58) Field of Classification Search
USPC .............................................. 340/604, 870.07
See application file for complete search history.

(56) References Cited

U.S. PATENT DOCUMENTS

| | | |
|---|---|---|
| 2005/0156744 A1 | 7/2005 | Pires |
| 2008/0036614 A1* | 2/2008 | Gabriel .................. A61F 13/42 |
| | | 340/604 |
| 2008/0243099 A1 | 10/2008 | Tippey et al. |
| 2011/0263952 A1 | 10/2011 | Bergman et al. |
| 2011/0295619 A1 | 12/2011 | Tough |
| 2012/0268278 A1 | 10/2012 | Lewis et al. |
| 2012/0323194 A1* | 12/2012 | Suzuki .................... A61F 5/451 |
| | | 604/361 |

FOREIGN PATENT DOCUMENTS

| | | |
|---|---|---|
| JP | 2006-504976 | 2/2006 |
| JP | 2011-147504 | 8/2011 |
| JP | 2012-105839 A | 6/2012 |
| JP | 2013-39158 A | 2/2013 |
| WO | WO-96/14813 A1 | 5/1996 |
| WO | WO-00/00144 A2 | 1/2000 |
| WO | WO 2004/038342 | 5/2004 |
| WO | WO-2004/100763 A2 | 11/2004 |
| WO | WO-2006/047815 A1 | 5/2006 |
| WO | WO-2011/054045 A1 | 5/2011 |
| WO | WO-2011/156862 A1 | 12/2011 |
| WO | WO-2014/146693 A1 | 9/2014 |

* cited by examiner

MONITORING AND DISPLAYING AN ABSORPTION STATE OF AN ABSORBENT ARTICLE

CROSS-REFERENCE TO PRIOR APPLICATION

This application is a §371 National Stage Application of PCT International Application No. PCT/EP2013/059045 filed Apr. 30, 2013, which is incorporated herein in its entirety.

TECHNICAL FIELD

The disclosure relates to a method of monitoring an absorption state of an absorbent article, such as a diaper, a sanitary towel, an incontinence garment, a medical dressing or the like, and a logger unit for performing this method. Further, the disclosure relates to methods of processing data indicating an absorption state of an absorbent article and to data processing units for performing these methods.

TECHNICAL BACKGROUND

Absorbent articles, such as diapers, sanitary towels, incontinence garments, medical dressings and the like, have widespread utility in both domestic and institutional settings for such purposes as the care of infants, the management of menstrual discharge, the management of bodily efflux or exudate and the management of incontinence. However, a known problem associated with the use of absorbent articles is that the articles have a finite capacity for absorption which, if exceeded, will cause the absorbent article to become ineffective, e.g., to leak, or at least to fail to absorb further.

Therefore, users of such articles, or their carers, must predict when an absorbent article is nearing its absorbent capacity and must then take steps to replace the article before capacity is reached. In situations where there are many users of such absorbent articles but relatively fewer carers, such as in institutional settings, the management of the capacity of the various absorbent articles in use becomes a significant administrative burden.

Since absorbent articles are available in a variety of absorbent capacities, the user or carer must also determine, from those products which are available, which capacity of article to select. For example, in some circumstances it may be preferable to select an article of a lower capacity which is changed more frequently in contrast to an article of relatively larger capacity which is changed less frequently. Factors influencing this choice will be the nature of the absorption required, i.e., whether intermittent large quantities or a continuous smaller rate, as well as the total volume expected to be absorbed during a given period of time.

It can be very difficult for a user or carer to accurately predict or determine the state of an absorbent article, in terms both of utilised absorbent capacity and the need for the article to be replaced. Even where the absorbent demands on the article are reasonably predictable, a period of record-keeping and experimentation is required before a pattern may be established, and appropriate absorbent articles provided.

Systems which are able to alert the user or carer to saturation or impending saturation of the absorbent article are therefore of benefit. Furthermore, systems which are able to monitor the usage pattern of a particular absorbent article, and of a series of absorbent articles associated with a particular individual, over a period of time, are of particular benefit.

Such systems may take the form of an absorbent article having embedded sensors which connect to a logger unit to monitor and record the sensor data over time. The sensors can, for example, be moisture sensors. When the absorbent capacity of the absorbent article is approached or exceeded, the user or the carer can be notified, on the basis of the recorded sensor data, that the absorbent article requires replacement.

Additionally, data obtained from a particular user over time can be used to monitor both the health of the user and the appropriateness of the absorbent article for that user over an extended period and can be used to provide better information for the care of the user. For example, an event, such as an incontinence event, leading to saturation of the article can be predicted and action, such as toileting action, taken before the event occurs.

Figure 1:
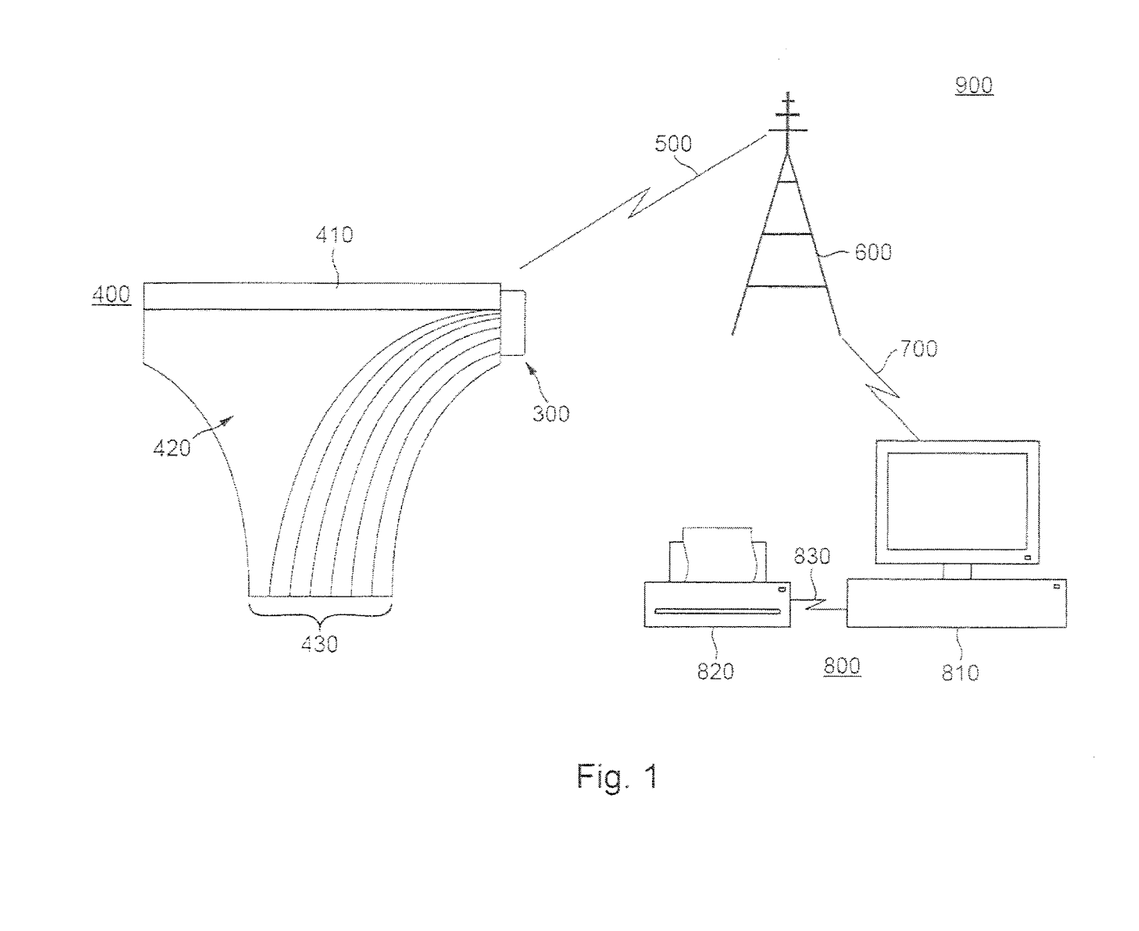
FIG. 1 is a schematic view of a monitoring system for absorbent articles.

One exemplary system is shown in FIG. 1, in which an absorbent article 400, exemplified here as a diaper and having a waistband 410 and an absorbent area 420, is provided with a logger unit 300 attached to the waistband 410 and having sense wires 430 extending from the logger unit 300 running through the absorbent area. The sense wires 430 may be used to detect moisture, for example by detecting changes in the conductivity between the wires. The sense wires may be only partly exposed to the absorbent area, for example by providing insulation, to localise the region of sensing. The particular wiring pattern depicted is wholly exemplary, and will be selected according to the sensing requirements.

The logger unit 300, including data-logging electronics such as a power source, processor, memory, instruction store, data store, communications bus, and data link interface, which cooperate to store, process, and/or forward the data derived from sense wires, is connected by data link 500 to a data receiver 600. In the example of FIG. 1, data link 500 is a wireless data link, and data receiver 600 is a wireless data receiver. However, it is also possible that a docking functionality can be provided between the logger 300 and a docking station functioning as data receiver 600 to transfer data recorded in the logger unit 300 when the logger unit 300 is placed into the docking station. In a further alternative, data link 500 can be provided over the cellular telephone network, in which case data receiver 600 may be implemented as a cellular base station.

The data received at data receiver 600 is then transmitted by a further data link 700 to data processing equipment 800, exemplified as computer terminal 810 and output device 820 mutually connected by data link 830. Here, the computer terminal 810, which is an example of a general purpose data processing device, conducts processing on the sensor data received from the logger unit 300 via data links 500 and 700 and data receiver 600 and takes action based on the same, for example by outputting alerts, predictions, or statistics via output device 820. Here, the output device is shown as a line printer, but could, for example, be another form of hard copy printer, a visual display unit, a visual alarm panel, or an audio output device, without limitation.

Such a system may provide a powerful tool for the management of users of absorbent articles.

However, absorbent articles are conventionally disposable absorbent articles for reasons of hygiene and convenience. Although reusable absorbent articles are known, they are rarely used, especially in institutional and clinical settings, for reasons of economy and hygiene, amongst others.

Therefore, in the arrangement of FIG. 1, if the logger unit 300 is directly connected to sensor wires 430, which extend through the article 400, when the absorbent article 400 is to be discarded after a use, the logger unit 300 must be discarded also. As the logger unit 300 is generally far more costly than the article 400 to manufacture, it is advantageous to provide the absorbent article 400 with a receptacle for receiving the ends of the sensor wires 430 at conductive terminals, and for accommodating the logger unit in a manner which permits the conductive terminals of the receptacle to contact corresponding conductive terminals of the logger unit when the logger unit is engaged with the receptacle. Such an arrangement is disclosed in Applicants' International Patent Application PCT/EP2013/055686, which was filed on 19 Mar. 2013. In this manner, when an absorbent article is ready for disposal, the datalogger can simply be disengaged from the receptacle by the care giver, and then engaged with the receptacle attached to the new absorbent article. This ensures that, when a new diaper is provided to an end user, the same logger is used so there is no potential for confusion regarding which data pertains to which end user.

WO-A-2011/054045 discloses a system for monitoring incontinence in one or more subjects wearing an absorbent article. In this system, a sensor monitors changes in resistance between electrodes provided in the absorbent article to identify the presence of wetness in the absorbent article. The magnitude of the change in resistance is detectable by a transmitter couplable with the sensor which, in use, transmits a continence-related data signal to a processor. The sensor may use a range of indicators to generate a continence-related data signal, such as changes in temperature, capacitance, inductance, impedance, presence of biological specimens, gases etc. Hence, in the system of WO-A-2011/054045, continence-related data is produced and transmitted only if a particular event, such as the presence of wetness in the absorbent article, occurs. It cannot be determined from the data thus obtained whether the absence of continence-related data for a certain time interval is due to the absence of such events or indicators or due to a failure or malfunction of the system. Therefore, such failures or malfunctions may be difficult to detect.

Hence, there remains a need for methods of monitoring an absorption state of an absorbent article and methods of processing data indicating this absorption state which allow for a reliable and efficient detection of such failures, as well as for devices for performing these methods.

SUMMARY

It is desired to provide devices for and methods of monitoring an absorption state of an absorbent article and of processing data indicating an absorption state of an absorbent article allowing for reliable and efficient failure detection.

Disclosed herein is a method of monitoring an absorption state of an absorbent article. The method includes providing a logger unit, acquiring, obtaining, detecting or measuring the absorption state of the absorbent article and recording data indicating the acquired absorption state of the absorbent article in the logger unit. Acquiring the absorption state of the absorbent article and recording the data indicating the acquired absorption state of the absorbent article in the logger unit are each continuously performed during or substantially during a monitoring period of the absorbent article.

Herein, the expressions "continuous" and "continuously" mean "in an uninterrupted, persistent and/or sustained manner". In particular, the expression "continuously acquiring the absorption state of the absorbent article" defines that this acquisition is performed by a persistent and/or sustained acquisition process. The absorption state of the absorbent article is acquired, obtained, detected or measured by continuous sampling, such as continuous analogue sampling or continuous digital sampling. The acquisition process may be performed by continuous sampling, e.g., digital sampling, with preset, predefined or predetermined sampling intervals, e.g., time intervals such as 1 s, 2 s, 4 s etc.

The monitoring period of the absorbent article may be a wear period of the absorbent article, i.e., a period in which the absorbent article is worn by a user. Acquiring the absorption state of the absorbent article and recording the data indicating the acquired absorption state of the absorbent article in the logger unit may be each continuously performed throughout or substantially throughout the entire wear period of the absorbent article.

The logger unit may be provided remote or at a distance from the absorbent article.

The logger unit may be provided attached, connected, mounted or secured to the absorbent article.

Acquiring the absorption state of the absorbent article and recording the data indicating the acquired absorption state of the absorbent article in the logger unit may be each continuously performed while the logger unit is attached to the absorbent article.

The method may include attaching, connecting, mounting or securing the logger unit to the absorbent article.

The absorption state of the absorbent article is continuously acquired and the data indicating the acquired absorption state of the absorbent article is continuously recorded in the logger unit during or substantially during the monitoring period of the absorbent article. The data recorded in the logger unit is thus continuous data covering the entire monitoring period. The data may be recorded continuously with preset, predefined or predetermined sampling intervals, e.g., time intervals such as 1 s, 2 s, 4 s etc.

Since acquiring the absorption state of the absorbent article and recording the data indicating the acquired absorption state of the absorbent article in the logger unit are each continuously performed, any gap which may occur in the data recorded in the logger unit can be reliably attributed to a failure or malfunction of the logger unit or related equipment, such as sensor elements in the absorbent article. Hence, such a failure or malfunction, e.g., caused by a cut in the power supply, for example, due to a low battery, or by a disconnection or detachment of the logger unit from the absorbent article, can be detected or identified in a reliable, efficient and quick manner.

The data recorded in the logger unit provides a variety of different types of information, namely information on the occurrence or presence of an absorption event, e.g., a wetting or incontinence event, information on the absence of such an absorption event and information on a failure of the absorption state acquiring and/or data recording process. In particular, the continuous acquisition of the absorption state and the continuous recording of data indicating the acquired absorption state allow for a distinction between the case that no absorption event has occurred and the case that there was a failure in the acquisition and/or recording process. Thus, the data recorded in the logger unit not only provides information on the occurrence of a system failure or malfunction, but further allows for the extent or degree of this failure or malfunction, i.e., for the time period in which no acquisition of the absorption state and/or recording of data was performed, to be accurately quantified. Therefore, it can be reliably and efficiently determined how large a fraction of the data is missing due to the failure or malfunction. On the basis of this information, the quality, significance and/or informative value of the data recorded in the logger unit can be accurately assessed.

Acquiring the absorption state of the absorbent article may be performed in use, e.g., only in use, of the absorbent article.

The absorbent article may be a diaper, a sanitary towel, an incontinence garment, an incontinence pad, a medical dressing or the like.

In one embodiment, the absorbent article has one or more sensor elements. Acquiring the absorption state of the absorbent article may be performed by means of the one or more sensor elements. Providing the logger unit may include connecting the logger unit to the one or more sensor elements. The connection between the logger unit and the one or more sensor elements may be of any suitable type.

In one embodiment, the logger unit is electrically connected to the one or more sensor elements.

However, connection and disconnection events between the logger unit and the one or more sensor elements can also refer to establishment and dis-establishment of an operative contactless connection between the logger unit and one or more remote sensors. For example, a sensor, such as moisture sensor or a gas sensor, can be provided in the form of a passive resonant circuit coupled to an antenna, whose resonant electrical characteristics, for example resonant frequency, will change with sensor state. A connection or disconnection event, in such a case, can include detection by the logger unit of whether such a circuit is near, for example, whether the logger unit has been brought near to such a circuit to form an operative connection such that the state of the resonant circuit may be determined.

Alternatively, the one or more sensors can be provided in the form of one or more active electrical circuits coupled to one or more antennas, for example RFID tags, and the connection or disconnection event, in such a case, can include detection by the logger unit whether such a circuit or circuits are sufficiently near for communication.

In each case, the connection or disconnection is such as to cause a change in state of an electrical circuit of the logger unit that is responsive to an external event. All such arrangements are considered to be within the scope of the terms connection and disconnection event as used herein.

The electronic equipment for determining the absorption state of the absorbent article may be provided in the logger unit and/or the one or more sensor elements. The one or more sensor elements may be one or more moisture sensor elements. The one or more sensor elements may be sensor electrodes, e.g., sense wires, such as the sense wires 430 shown in FIG. 1.

The method may further include detaching the logger unit from the absorbent article.

In one embodiment, the method further includes attaching the logger unit to a reading unit, e.g., a docking station or the like, e.g., after removal or detachment from the absorbent article. The data stored in the logger unit can be read out by the reading unit. The read out data may be sent to a data processing unit or the like for processing thereof, e.g., by wireless transmission or communication.

In one embodiment, the method further includes transmitting the data recorded in the logger unit to a location remote of the logger unit, such as a data processing unit. Transmitting the data recorded in the logger unit may be performed by wireless transmission, for example, over the cellular telephone network. Transmitting the data recorded in the logger unit may be performed while the logger unit is connected to the one or more sensor elements of the absorbent article, for example, while the logger unit is attached to the absorbent article, or after the logger unit has been disconnected from the one or more sensor elements, for example, after detachment from the absorbent article.

The data stored in the logger unit may be transmitted to a location remote of the logger unit in a single data transmission process, transmitting all the data recorded in the logger unit. Alternatively, transmitting the data recorded in the logger unit may be performed by batch transmission, sequentially transmitting portions of the recorded data.

In one embodiment, the data recorded in the logger unit is transmitted to the location remote of the logger unit in preset, predefined or predetermined intervals. In particular, the data recorded in the logger unit may be transmitted to the location remote of the logger unit in preset, predefined or predetermined time intervals. In this case, data recorded in the logger unit may be transmitted over a preset period of time. Subsequently, data transmission may be stopped for a preset period of time. Such a cycle of starting and stopping the data transmission may be repeated one or more times.

The data recorded in the logger unit may be transmitted to the location remote of the logger unit in preset, predefined or predetermined data intervals, i.e., intervals defined by preset, predefined or predetermined amounts of data recorded in the logger unit. For example, once a preset, predefined or predetermined amount of data has been recorded in the logger unit, the data may be transmitted to the location remote of the logger unit. This process may be repeated one or more times.

If the data transmission is not possible, e.g., due to bad or no signal reception, at a certain point in time, acquiring the absorption state of the absorbent article and recording data indicating the acquired absorption state can still be continuously performed, so that no data is lost. In this case, data transmission may be attempted again at a later point in time, e.g., once the signal reception has sufficiently improved.

In one embodiment, the method further includes determining whether data indicating the acquired absorption state of the absorbent article has been recorded in the logger unit throughout the entire monitoring period. In this way, gaps in the data, indicating a failure or malfunction of the logger unit or the equipment related thereto, such as the one or more sensor elements of the absorbent article, can be reliably identified. Further, based on the amount of missing data, the quality, significance and/or informative value of the data recorded in the logger unit can be accurately assessed.

The method may include determining whether data indicating the acquired absorption state of the absorbent article has been correctly or properly recorded in the logger unit throughout the entire monitoring period.

In one embodiment, the method further includes marking the data recorded in the logger unit as inaccurate or unreliable if it is determined that data indicating the acquired absorption state of the absorbent article has not been recorded in the logger unit throughout the entire monitoring period.

In one embodiment, the method further includes an interpolation process if it is determined that data indicating the acquired absorption state of the absorbent article has not been recorded in the logger unit throughout the entire monitoring period. The interpolation process may include interpolating values for the absorption state in the time interval or intervals in which no data indicating the acquired absorption state of the absorbent article has been recorded in the logger unit, on the basis of the data recorded in the logger unit. In this way, the missing data can be compensated for in an efficient manner. Hence, the resulting set of data, including the interpolated values for the absorption state, may be used as a reliable basis for an accurate assessment of the absorption state of the absorbent material.

The absorption state may be a saturation state or an absorption level of the absorbent article. The absorption state may include the amount and/or volume of liquid absorbed in the absorbent article and/or the point in time at which liquid absorption in the absorbent article has started to occur and/or stopped to occur and/or the duration over which liquid absorption in the absorbent article has occurred and/or the distribution, e.g., the spatial distribution, of absorbed liquid in the absorbent article. The absorption state may include the number of segments, portions and/or zones of the absorbent article which have absorbed liquid, e.g., the number of wetted segments, portions and/or zones of the absorbent article.

In one embodiment, the method further includes establishing an absorption pattern, e.g., an absorption profile, on the basis of the data recorded in the logger unit. The absorption pattern may be a time pattern, indicating the time dependent absorption process in the absorbent article, and/or a spatial pattern, indicating the spatial distribution of absorbed liquid in the absorbent article. For example, if the absorbent article is a diaper, an incontinence garment, an incontinence pad or the like, such an absorption pattern allows for the toileting, wetting or incontinence behaviour of the subject or user wearing the absorbent article to be determined. Thus, the process of changing the absorbent article can be optimised in terms of frequency and timing. Moreover, such an absorption pattern can aid in selecting the most suitable type of absorbent article, e.g., in terms of absorbent capacity, shape etc.

In one embodiment, the method further includes displaying or presenting the data recorded in the logger unit in continuous, i.e., uninterrupted, form. Such a continuous display or presentation of the recorded data allows for the presence of gaps in the data, indicating a failure of the process of acquiring the absorption state and/or the process of data recording, to be identified in a reliable and simple manner.

The method may further include collating the data recorded in the logger unit so as to obtain a single continuous data set.

A logger unit for monitoring an absorption state of an absorbent article is also disclosed. The logger unit is configured to acquire, obtain, detect or measure the absorption state of the absorbent article. The logger unit is configured to record therein, i.e., in the logger unit, data indicating the acquired absorption state of the absorbent article. The logger unit is configured so that acquiring the absorption state of the absorbent article and recording the data indicating the acquired absorption state of the absorbent article in the logger unit are each continuously performed during or substantially during a monitoring period of the absorbent article.

The monitoring period of the absorbent article may be a wear period of the absorbent article, i.e., a period in which the absorbent article is worn by a user. The logger unit may be configured so that acquiring the absorption state of the absorbent article and recording the data indicating the acquired absorption state of the absorbent article in the logger unit are each continuously performed throughout or substantially throughout the entire wear period of the absorbent article.

The logger unit may have a means for attachment or connection to the absorbent article, such as a clip, a hook, a Velcro fastener or the like. The logger unit may be configured to acquire, obtain, detect or measure the absorption state of the absorbent article when the logger unit is attached or connected to the absorbent article.

The logger unit may be configured so that acquiring the absorption state of the absorbent article and recording the data indicating the acquired absorption state of the absorbent article in the logger unit are each continuously performed while the logger unit is attached to the absorbent article.

The logger unit may include an acquisition unit or a detection unit which is configured to acquire, obtain, detect or measure the absorption state of the absorbent article.

The acquisition unit or detection unit may be configured to acquire, obtain, detect or measure the absorption state of the absorbent article when the logger unit is attached to the absorbent article.

The logger unit may include a recording unit, such as a memory, e.g., RAM and/or flash, or the like, which is configured to record therein data indicating the acquired absorption state of the absorbent article.

The logger unit may be configured to be activated or switched on, e.g., automatically activated or switched on, when it is connected to the one or more sensor elements, e.g., when it is attached to the absorbent article.

The logger unit may be configured to be deactivated or switched off, e.g., automatically deactivated or switched off, when it is disconnected from the one or more sensor elements, e.g., when it is removed or detached from the absorbent article.

In one embodiment, the logger unit is configured to transmit the data recorded therein, e.g., in a recording unit, such as a memory, to a location remote of the logger unit, such as a data processing unit. The logger unit may be configured to transmit the data recorded therein to the location remote of the logger unit in preset, predefined or predetermined intervals, e.g., time intervals or data intervals.

The logger unit may be configured to determine whether data indicating the acquired absorption state of the absorbent article has been recorded in the logger unit throughout the entire monitoring period.

The logger unit may be configured to mark the data recorded in the logger unit as inaccurate if it is determined that data indicating the acquired absorption state of the absorbent article has not been recorded in the logger unit throughout the entire monitoring period.

The logger unit may be configured to perform an interpolation process if it is determined that data indicating the acquired absorption state of the absorbent article has not been recorded in the logger unit throughout the entire monitoring period. The interpolation process may include interpolating values for the absorption state in the time interval or intervals in which no data indicating the acquired absorption state of the absorbent article has been recorded in the logger unit, on the basis of the data recorded in the logger unit.

The logger unit may include an interpolation unit which is configured to perform such an interpolation process.

The logger unit described herein provides the advantageous effects already described in detail above for the disclosed method. In particular, the logger unit allows for reliable and efficient failure detection.

The logger unit can be a device for performing the disclosed method. Hence, the further features disclosed in connection with the above description of the method may also be applied to the logger unit.

Also described is a combination of the logger unit and an absorbent article.

The absorbent article may have one or more sensor elements. The logger unit may be connectable to the one or more sensor elements. The logger unit may be configured to acquire the absorption state of the absorbent article by means of the one or more sensor elements. The one or more sensor elements may be configured as described above.

In one embodiment, the logger unit is electrically connectable to the one or more sensor elements.

However, connection and disconnection events between the logger unit and the one or more sensor elements can also refer to establishment and dis-establishment of an operative contactless connection between the logger unit and one or more remote sensors as has been detailed above.

Also described is a method of processing data indicating an absorption state of an absorbent article. The method includes receiving sets of data indicating the absorption state of the absorbent article, wherein each of the sets of data indicates the absorption state of the absorbent article over a portion of a continuous period of time, and displaying or presenting the sets of data in continuous, i.e., uninterrupted, form for the entire continuous period of time. Such a continuous display or presentation of the sets of data allows for gaps in the data to be reliably and quickly identified, thereby enabling reliable and efficient failure detection.

The sets of data indicating the absorption state of the absorbent article may be provided by the logger unit, e.g., by wireless transmission or through a reading unit or the like. In particular, the logger unit may transmit the data recorded therein in preset intervals, e.g., time or data intervals, the data transmitted in each interval corresponding to a set of data received in the data processing method.

Also described is a method of processing data indicating an absorption state of an absorbent article. The method includes receiving sets of data indicating the absorption state of the absorbent article, wherein each of the sets of data indicates the absorption state of the absorbent article over a portion of a continuous period of time, and collating the sets of data so as to obtain a single set of data indicating the absorption state of the absorbent article over the continuous period of time. By providing such a single set of continuous data, the process of identifying gaps in the data, indicating a failure in data acquisition and/or recording, is facilitated in a simple and reliable manner.

The sets of data indicating the absorption state of the absorbent article may be provided by the logger unit, e.g., by wireless transmission or through a reading unit or the like. In particular, the logger unit may transmit the data recorded therein in preset intervals, e.g., time or data intervals, the data transmitted in each interval corresponding to a set of data received in the data processing method.

The method may further include displaying the single set of data in continuous, i.e., uninterrupted, form. In this way, a continuous report on the absorption state of the absorbent article can be presented.

The methods of processing data may further include displaying time intervals, e.g., gaps, in the data in which no indication on the absorption state of the absorbent article is provided. In this way, failures in data acquisition and/or recording can be identified in a particularly reliable and efficient manner.

The methods of processing data may further include displaying the number of segments, portions and/or zones of the absorbent article which have absorbed liquid, e.g., the number of wetted segments, portions and/or zones of the absorbent article. From this number, the amount and/or volume of absorbed liquid can be determined or calculated in a simple and reliable manner, thus allowing for a wetting or incontinence event to be accurately quantified.

The methods of processing data may further include a data selection process, e.g., by a user, i.e., a process of selecting the data to be displayed from the one or more sets of data. The data to be displayed may be selected from the one or more sets of data, e.g., based on data selection information by a user, and the selected data may be displayed. Thus, for example, in the case that the data displayed contains data which is not of interest to the user, the user may perform a data selection process as detailed above, selecting only the data of interest for display.

Also disclosed is a data processing unit for processing data indicating an absorption state of an absorbent article. The data processing unit is configured to receive sets of data indicating the absorption state of the absorbent article, wherein each of the sets of data indicates the absorption state of the absorbent article over a portion of a continuous period of time. The data processing unit is further configured to display the sets of data in continuous form for the entire continuous period of time.

The sets of data indicating the absorption state of the absorbent article may be provided by the logger unit, e.g., by wireless transmission or through a reading unit or the like. In particular, the logger unit may transmit the data recorded therein in preset intervals, e.g., time or data intervals, the data transmitted in each interval corresponding to a set of data received by the data processing unit.

The data processing unit may be configured to determine whether data indicating the acquired absorption state of the absorbent article has been recorded in the logger unit throughout the entire monitoring period.

The data processing unit may be configured to mark the data recorded in the logger unit and transmitted to the data processing unit as inaccurate if it is determined that data indicating the acquired absorption state of the absorbent article has not been recorded in the logger unit throughout the entire monitoring period.

The data processing unit may be configured to perform an interpolation process if it is determined that data indicating the acquired absorption state of the absorbent article has not been recorded in the logger unit throughout the entire monitoring period. The interpolation process may include interpolating values for the absorption state in the time interval or intervals in which no data indicating the acquired absorption state of the absorbent article has been recorded in the logger unit, on the basis of the data recorded in the logger unit.

The data processing unit may include an interpolation unit which is configured to perform such an interpolation process.

Also described is a data processing unit for processing data indicating an absorption state of an absorbent article. The data processing unit is configured to receive sets of data indicating the absorption state of the absorbent article, wherein each of the sets of data indicates the absorption state of the absorbent article over a portion of a continuous period of time. The data processing unit is further configured to collate the sets of data so as to obtain a single set of data indicating the absorption state of the absorbent article over the continuous period of time.

The data processing unit may be further configured to display the single set of data in continuous form.

The sets of data indicating the absorption state of the absorbent article may be provided by the logger unit, e.g., by wireless transmission or through a reading unit or the like. In particular, the logger unit may transmit the data recorded therein in preset intervals, e.g., time or data intervals, the data transmitted in each interval corresponding to a set of data received by the data processing unit.

The data processing unit may be configured to determine whether data indicating the acquired absorption state of the absorbent article has been recorded in the logger unit throughout the entire monitoring period.

The data processing unit may be configured to mark the data recorded in the logger unit and transmitted to the data processing unit as inaccurate if it is determined that data indicating the acquired absorption state of the absorbent article has not been recorded in the logger unit throughout the entire monitoring period.

The data processing unit may be configured to perform an interpolation process if it is determined that data indicating the acquired absorption state of the absorbent article has not been recorded in the logger unit throughout the entire monitoring period. The interpolation process may include interpolating values for the absorption state in the time interval or intervals in which no data indicating the acquired absorption state of the absorbent article has been recorded in the logger unit, on the basis of the data recorded in the logger unit.

The data processing unit may include an interpolation unit which is configured to perform such an interpolation process.

The data processing units may be configured to display time intervals, e.g., gaps, in the data in which no indication on the absorption state of the absorbent article is provided. In this way, failures in data acquisition and/or recording can be identified in a particularly reliable and efficient manner.

The data processing units may be configured to display the number of segments, portions and/or zones of the absorbent article which have absorbed liquid, e.g., the number of wetted segments, portions and/or zones of the absorbent article. From this number, the amount and/or volume of absorbed liquid can be determined or calculated in a simple and reliable manner, thus allowing for a wetting or incontinence event to be accurately quantified.

The data processing units may be configured to allow for a data selection, e.g., by a user, i.e., a selection of the data to be displayed from the one or more sets of data. The data processing units may have a user interface, e.g., including an input element which is configured to receive input information from a user. The input element may be, for example, a button, a switch, a touch panel, an accelerometer, a light level sensor or the like. The input element may be configured to receive data selection information from a user. The data processing units may be configured to select the data to be displayed from the one or more sets of data based on the input data selection information and to display the selected data. Thus, for example, in the case that the data displayed by the data processing unit contains data which is not of interest to the user, the user may perform a data selection as detailed above, instructing the data processing unit via the user interface, e.g., through the input element, only to display the data of interest.

The data processing units provide the advantageous effects already described above for the methods. In particular, the data processing units allow for reliable and efficient failure detection.

The data processing units are devices for performing the data processing methods. Hence, the features disclosed in connection with the description of the data processing methods may also be applied to the data processing units and vice versa.

BRIEF DESCRIPTION OF THE DRAWINGS

Hereinafter, non-limiting examples of embodiments of the invention are explained with reference to the drawings, in which.

DETAILED DESCRIPTION OF PARTICULAR EMBODIMENTS

Figure 2:
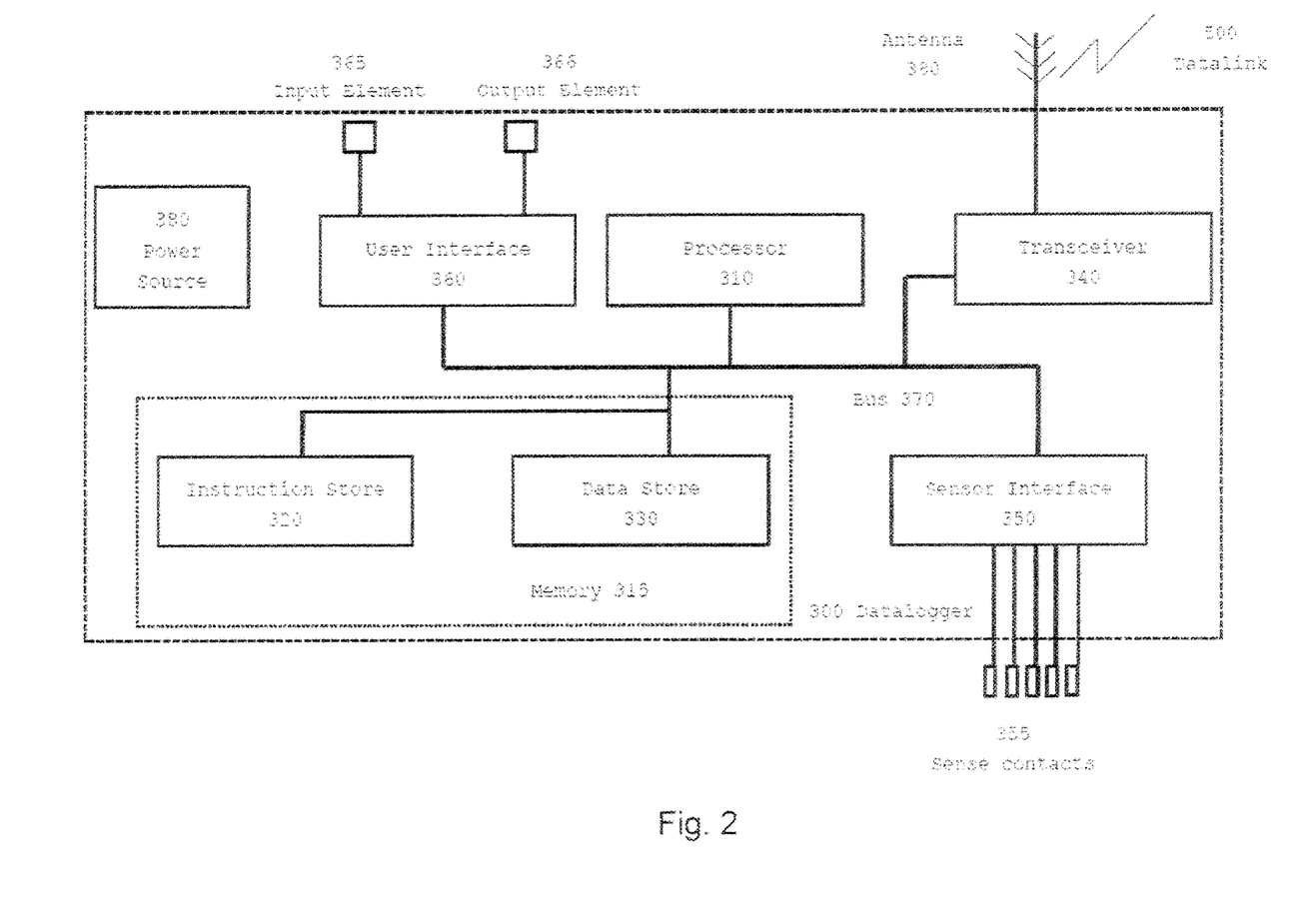
FIG. 2 is a schematic diagram of a datalogger as an example of a logger unit.

FIG. 2 shows a schematic diagram of a datalogger 300 as an example of a logger unit.

It is important to understand that the configuration shown in FIG. 2 is purely exemplary, and the functionality provided by the arrangement of FIG. 2 may be provided in other ways, including using application specific integrated circuits (ASICs), general purpose data processors, discrete electronics, or other arrangements as are conventional in the art.

As an example of the configuration of data processing equipment which provides the functionality of datalogger 300, there is provided a processor 310, which derives instructions from instruction store 320, operates on data stored in data store 330, is able to transmit and receive data over data link 500 using transceiver 340 and antenna 345, is able to interface with sensor elements in the absorbent article, such as the sense wires 430 shown in FIG. 1, by means of sensor interface 350 and sense contacts 355, and is able to give and receive user interface events via user interface 360 connected to input element 365 and output element 366.

Processor 310, instruction store 320, data store 330, transceiver 340, sensor interface 350, and user interface 360 are connected by a common bus 370 and are all powered by power source 380.

The instruction store 320 and data store 330 may be implemented as a common memory 315, or may be implemented as individual memories.

Power source 380 can be provided, for example, as any suitable power source such as a lithium ion or nickel metal hydride rechargeable battery, or a user-replaceable zinc or alkaline battery.

Sensor interface 350 may be, for example, an analogue to digital convertor (ADC) configured to measure resistance, conductivity or capacitance between pairs of sense contacts 355, or may be a threshold sensing unit configured to detect when the resistance, conductivity or capacitance between pairs of sense contacts 355 drops below or rises above a predetermined level.

Aside from detecting resistance between sense contacts 355, sensor interface 350 may also be configured to detect, in combination with suitable active or passive sense elements as may be known in the art, other variables, parameters or properties, such as pH, temperature, and the presence or absence of certain compounds in the said absorbent article.

Input element 365 may be, for example, a button, a switch, a touch panel, an accelerometer, or a light level sensor, while output element 366 may be, for example, a visible indicator such as a lamp or LED; an audible indicator such as a sounder, buzzer, beeper, or loudspeaker; or a tactile indicator, such as a vibrator.

Figure 3:
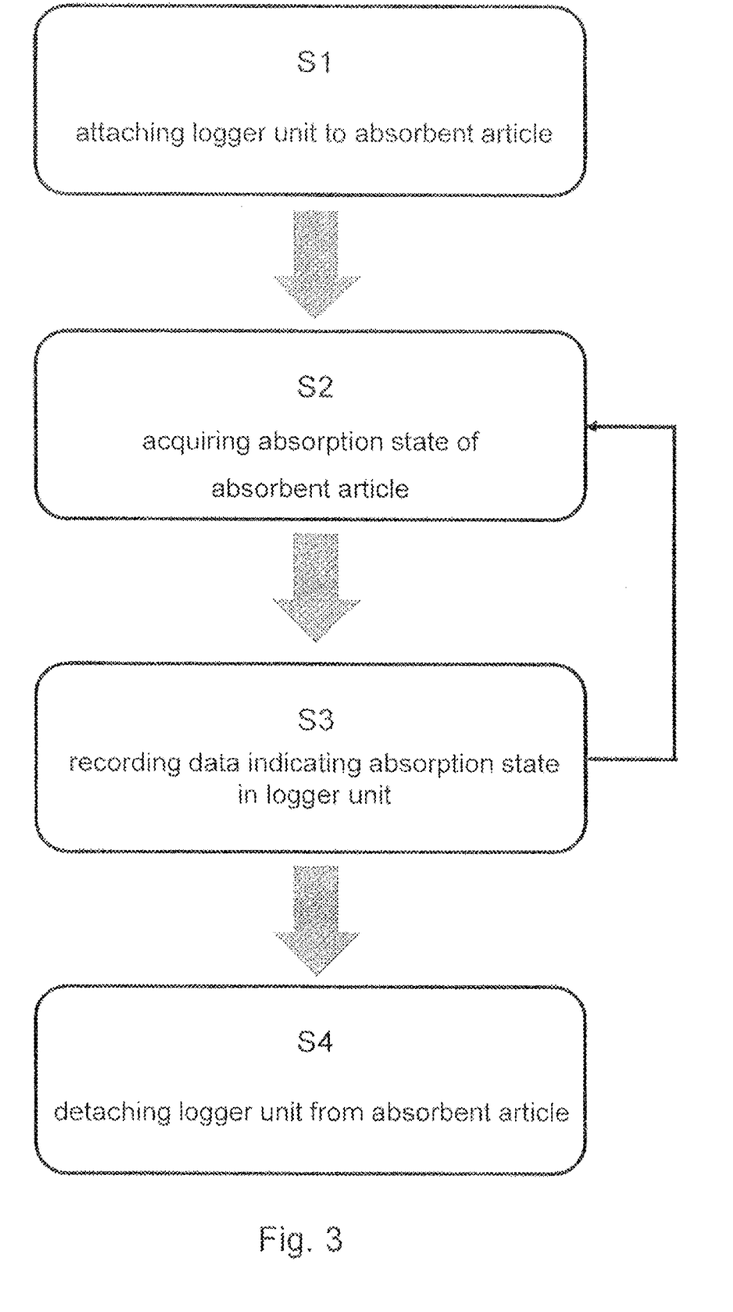
FIG. 3 is a schematic diagram of an embodiment of a monitoring method.

One mode of operation of the datalogger 300, exemplifying an embodiment of a monitoring method, will now be described with reference to FIG. 3.

First, the datalogger 300 is attached to an absorbent article (S1), such as the absorbent article 400 shown in FIG. 1. Attachment of the datalogger 300 to the absorbent article 400 is performed by use of an attachment means (not shown) provided on the datalogger 300, such as a clip, a hook, a Velcro fastener or the like. When attaching the datalogger 300 to the absorbent article 400, the datalogger 300 is electrically connected to sensor elements in the absorbent article 400, such as the sense wires 430 shown in FIG. 1.

The datalogger 300 is configured to automatically start acquiring the absorption state of the absorbent article 400 and recording data indicating the acquired absorption state of the absorbent article in the datalogger 300 as soon as an electrical connection between the sense contacts 355 and the sense wires 430 has been established. Specifically, subsequently, the datalogger 300 acquires the absorption state of the absorbent article 400 through the sensor interface 350 (S2). Then, data indicating the acquired absorption state is recorded in the data store 330 (S3). The absorption state acquisition process S2 and the data recording process S3 are continuously performed, as indicated by the arrow leading from S3 to S2 on the right-hand side of FIG. 3, until the datalogger 300 is detached from the absorbent article 400 (S4).

In the above, connection and disconnection events have been described with reference to physical connection, i.e., attachment, or disconnection of the datalogger 300 with the absorbent article 400 or with reference to electrical connection or disconnection between contacts on the datalogger 300 and contacts on the absorbent article 400. However, connection and disconnection events between the datalogger 300 and the sensor elements can also refer to establishment and dis-establishment of an operative contactless connection between the datalogger and remote sensors. For example, a sensor, such as a moisture sensor or a gas sensor, can be provided in the form of a passive resonant circuit coupled to an antenna, whose resonant electrical characteristics, for example resonant frequency, will change with sensor state. A connection or disconnection event, in such a case, can include detection by the datalogger 300 of whether such a circuit is near, for example, whether the datalogger 300 has been brought near to such a circuit to form an operative connection such that the state of the resonant circuit may be determined.

Alternatively, the sensors can be provided in the form of active electrical circuits coupled to an antenna, for example an RFID tag, and the connection or disconnection event, in such a case, can include detection by the datalogger 300 whether such a circuit is sufficiently near for communication.

In each case, the connection or disconnection is such as to cause a change in state of an electrical circuit of the datalogger 300 that is responsive to an external event. All such arrangements are considered to be within scope of the terms connection and disconnection event as used herein.

The data recorded in the data store 330 is transmitted to a data processing unit 900 (see FIG. 4) in preset time intervals via the transceiver 340 and the antenna 380. Processing or pre-processing of the data stored in the data store 330 may be performed by the processor 310.

Figure 4:
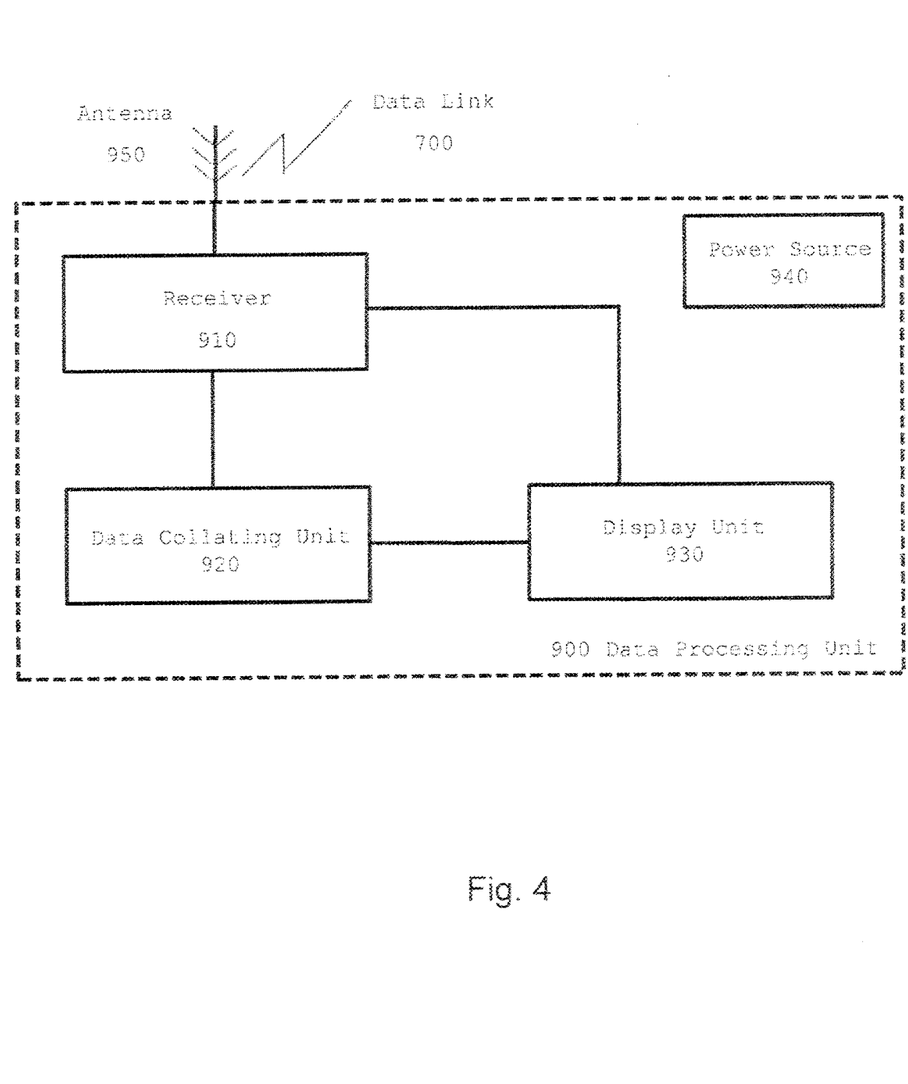
FIG. 4 is a schematic diagram of an embodiment of a data processing unit.

In particular, the processor 310 may determine whether data indicating the acquired absorption state of the absorbent article 400 has been recorded in the data store 330 throughout the entire time period in which the datalogger 300 was attached to the absorbent article 400. If the processor 310 identifies gaps in the data stored in the data store 330, it may mark the data recorded in the data store 330 as inaccurate or unreliable or perform an interpolation process including interpolating values for the absorption state in the time interval or intervals in which no data indicating the acquired absorption state of the absorbent article has been recorded in the data store 330, on the basis of the data recorded in the data store 330.

The datalogger 300 is further configured to be automatically deactivated when it is removed or detached from the absorbent article 400, i.e., when the sense contacts 355 are disconnected from the sense wires 430. In the embodiment shown in FIG. 2, the sensor interface 350 and the sense contacts 355 serve as an acquisition unit and the data store 330 serves as a recording unit.

FIG. 4 shows a schematic diagram of a data processing unit 900. It is important to understand that the configuration shown in FIG. 4 is purely exemplary, and the functionality provided by the arrangement of FIG. 4 may be provided in other ways.

The data processing unit 900 includes a receiver 910 which is configured to receive sets of data indicating the absorption state of the absorbent article 400 from the datalogger 300 via an antenna 950 and data link 700 (see FIG. 1). Each of the sets of data indicates the absorption state of the absorbent article 400 over a portion of a continuous period of time. In particular, the sets of data are provided by transmission from the datalogger 300 via the antenna 380 and data link 500 (see FIG. 1) in preset time intervals.

The data processing unit 900 further includes a data collating unit 920 configured to collate the sets of data so as to obtain a single set of data indicating the absorption state of the absorbent article 400 over the continuous period of time. Moreover, the data processing unit 900 includes a display unit 930 configured to display the sets of data or a single set of data, obtained by collating the sets of data in the data collating unit 920, in continuous form. In particular, as is schematically shown in FIG. 4, the data processing unit 900 is configured so that the sets of data received by the receiver 910 may be directly sent to the display unit 930 or, alternatively, the sets of data may be sent to the data collating unit 920, the sets of data may be collated in the data collating unit 920 so as to obtain a single set of data and, subsequently, the single set of data may be sent to the display unit 930.

The data collating unit 920 may be a processor, such as the CPU of a computer, or the like. The display unit 930 may be, for example, a line printer or another form of hard copy printer or a visual display unit, such as a display, a screen, a monitor or the like.

The receiver 910, the data collating unit 920 and the display unit 930 are all powered by the power source 940.

The power source 940 can be provided, for example, as any suitable power source such as a lithium ion or nickel metal hydride rechargeable battery, or a user-replaceable zinc or alkaline battery.

Figure 5:
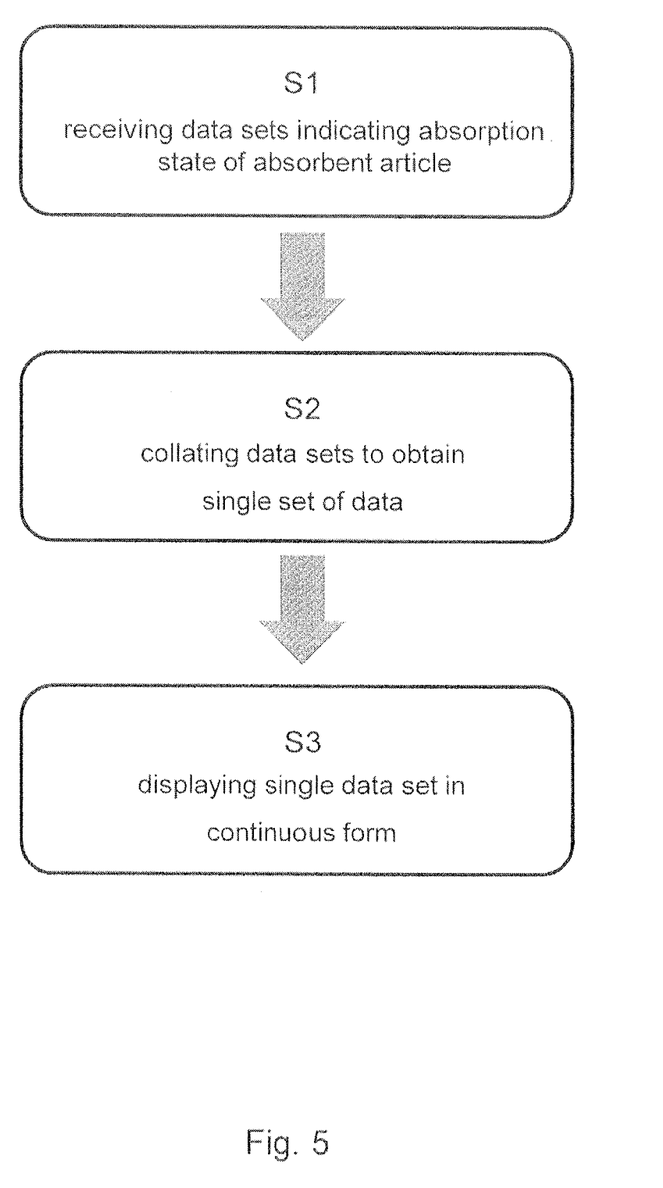
FIG. 5 is a schematic diagram of a data processing method.

One mode of operation of the data processing unit 900, exemplifying an embodiment of a data processing method, will now be described with reference to FIG. 5.

First, the receiver 910 receives sets of data indicating the absorption state of the absorbent article 400 from the datalogger 300 via the antenna 950 and data link 700 (see FIG. 1) through wireless communication (S1). The datalogger 300 transmits the data recorded in the data store 330 to the data processing unit 900 in preset time intervals. Thus, in each of these intervals a set of data indicating the absorption state of the absorbent article 400 is received by the receiver 910. Each of these sets of data indicates the absorption state of the absorbent article 400 over a portion of a continuous period of time, namely the period of time over which the datalogger 300 is attached to the absorbent article 400.

Then, the data sets received by the receiver 910 are sent to the data collating unit 920 and collated, so as to obtain a single set of data indicating the absorption state of the absorbent article 400 over the continuous period of time (S2). Subsequently, the single set of data obtained by the data collating unit 920 is sent to the display unit 930 and displayed by the display unit 930 in continuous, i.e., uninterrupted, form (S3).

Figure 6:
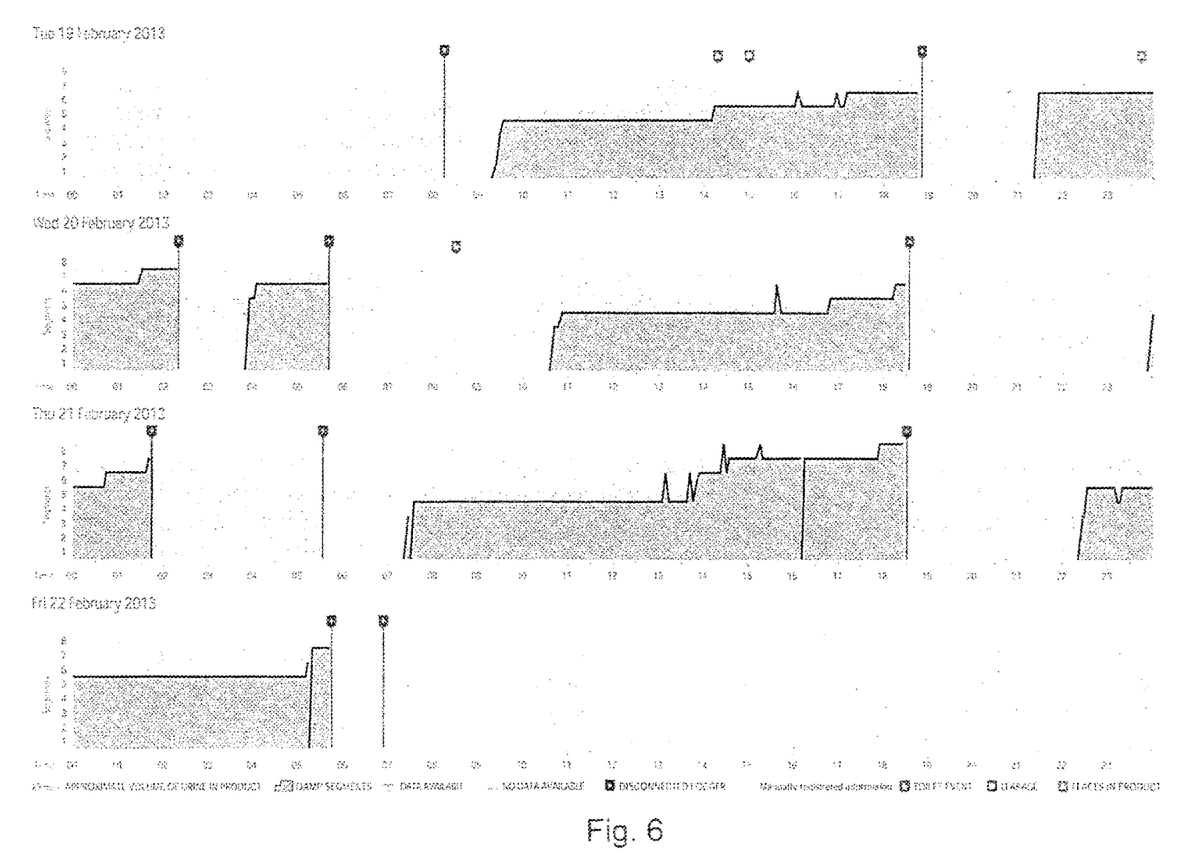
FIG. 6 is one example of a continuous report obtained by embodiments of the disclosed methods, showing the time dependent behaviour of the absorption state of an absorbent article.

FIG. 6 shows an example of continuous data indicating the absorption state of the absorbent article 400, worn by a user, over a continuous period of time, i.e., four consecutive days, as presented in continuous form by the display unit 930. FIG. 6 shows the time in hours on the X-axis (abscissa) and the number of segments of the absorbent article 400 on the Y-axis (ordinate). The different segments of the absorbent article 400 may be arranged, for example, between the different sense wires 430 shown in FIG. 1.

A damp or wet state of the absorbent article 400, i.e., an absorption state in which liquid has been absorbed by one or more segments of the absorbent article 400, is indicated by dark grey shading. The extension of the dark grey area along the Y-axis indicates the number of wetted segments of the absorbed article, i.e., the number of segments of the absorbed article which have absorbed liquid. From this number, the amount and/or volume of absorbed liquid can be determined or calculated in a simple and reliable manner, thus allowing for a wetting or incontinence event to be accurately quantified. A dry state of the absorbent article 400, i.e., an absorption state in which no liquid has been absorbed in any of the segments, is indicated by vertically alternating light grey and white horizontal lines. Gaps in the data, i.e., time periods for which no data indicating the absorption state of the absorbent article 400 is recorded in the data store 330, are indicated by white spaces along the X-axis.

As can be seen from FIG. 6, no such gaps are present in the data shown in this figure. Hence, it can be immediately taken from this continuous data that no failure in the absorption state acquisition and data recording processes has occurred and that this data allows for a reliable assessment of the absorption pattern, i.e., wetting pattern, of the wearer of the absorbent article 400. In particular, the data presented in FIG. 6 allows for the wetting pattern of the wearer of the absorbent article 400 to be reliably established, so that both the changing times of the absorbent article 400 and the type of absorbent article to be used can be tailored to the wearer's characteristic behaviour, i.e., wetting or incontinence behaviour, and needs.

Figure 7:
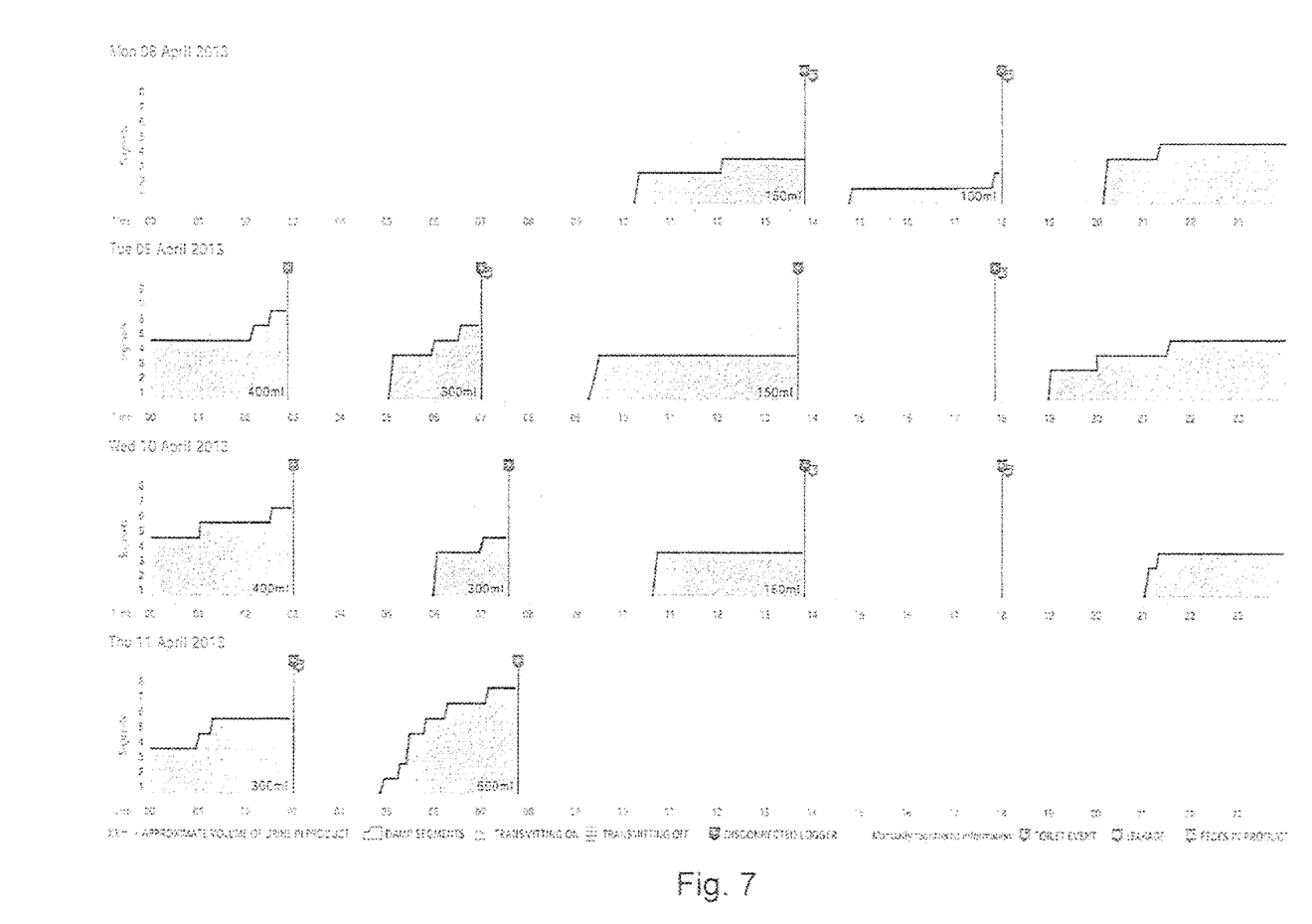
FIG. 7 is another example of a continuous report obtained by embodiments of the disclosed methods, showing the time dependent behaviour of the absorption state of an absorbent article.

FIG. 7 shows another example of continuous data indicating the absorption state of the absorbent article 400, worn by a different user, over another continuous period of time, i.e., four consecutive days, as presented in continuous form by the display unit 930. As can be seen from FIG. 7, the absorption pattern, i.e., wetting pattern, of this user differs substantially from that shown in FIG. 6, both in terms of the number and the volumes of the wetting events. Further, a number of white spaces along the X-axis, i.e., gaps in the data, can be identified, indicating time periods for which no data indicating the absorption state of the absorbent article 400 is recorded in the data store 330. For example, the gap at 7 hours in the second line from the top of FIG. 7 can be attributed to a toilet event, i.e., to the user visiting the toilet, thus disabling the datalogger 300.

Displaying these gaps in the continuous data of FIG. 7 allows for the time period in which no acquisition of the absorption state and/or recording of data was performed to be accurately quantified. Therefore, it can be reliably and efficiently determined how large a fraction of the data is missing. On the basis of this information, the quality, significance and/or informative value of the data recorded in the datalogger 300 can be accurately assessed.

The foregoing embodiments and their variants have been disclosed for illustrative purposes only, and further variation is wholly possible within the capabilities of the skilled reader. Accordingly, the appended claims are intended to cover all modifications, substitutions, alterations, omissions and additions which one skilled in the art could achieve from the foregoing disclosure, taking into account his own general and specialist knowledge and expertise.

The invention claimed is:

1. A method of monitoring an absorption state of an absorbent article, the method comprising
   providing a logger unit;
   acquiring the absorption state of the absorbent article;
   recording data indicating the acquired absorption state of the absorbent article in the logger unit; and
   determining whether data indicating the acquired absorption state of the absorbent article has been recorded in the logger unit throughout the entire monitoring period,
   wherein acquiring the absorption state of the absorbent article and recording the data indicating the acquired absorption state of the absorbent article in the logger unit are each continuously performed during a monitoring period of the absorbent article.

2. The method according to claim 1, wherein the absorbent article has one or more sensor elements;
   wherein acquiring the absorption state of the absorbent article is performed by the one or more sensor elements; and
   wherein providing the logger unit comprises connecting the logger unit to the one or more sensor elements.

3. The method according to claim 1, further comprising transmitting the data recorded in the logger unit to a location remote of the logger unit.

4. The method according to claim 3, wherein the data recorded in the logger unit is transmitted to the location remote of the logger unit in preset intervals.

5. The method according to claim 1, further comprising marking the data recorded in the logger unit as inaccurate if it is determined that data indicating the acquired absorption state of the absorbent article has not been recorded in the logger unit throughout the entire monitoring period.

6. The method according to claim 1, further comprising an interpolation process if it is determined that data indicating the acquired absorption state of the absorbent article has not been recorded in the logger unit throughout the entire monitoring period,
 wherein the interpolation process comprises interpolating values for the absorption state in the time interval or intervals in which no data indicating the acquired absorption state of the absorbent article has been recorded in the logger unit, on the basis of the data recorded in the logger unit.

7. The method according to claim 1, wherein the absorption state includes at least one of the group consisting of: the amount of liquid absorbed in the absorbent article; the volume of liquid absorbed in the absorbent article; the point in time at which liquid absorption in the absorbent article has started to occur; the point in time at which liquid absorption in the absorbent article has stopped to occur; the duration over which liquid absorption in the absorbent article has occurred; and the distribution of absorbed liquid in the absorbent article.

8. The method according to claim 1, further comprising establishing an absorption pattern on the basis of the data recorded in the logger unit.

9. The method according to claim 1, further comprising displaying the data recorded in the logger unit in continuous form.

10. A logger unit for monitoring an absorption state of an absorbent article, comprising
 a processor configured to acquire the absorption state of the absorbent article; and
 a memory configured to record therein data indicating the acquired absorption state of the absorbent article,
 wherein the processor and memory are configured to acquire the absorption state of the absorbent article and record the data indicating the acquired absorption state of the absorbent article in the logger unit continuously during a monitoring period of the absorbent article, and
 wherein the processor and memory are configured to determine whether data indicating the acquired absorption state of the absorbent article has been recorded in the logger unit throughout the entire monitoring period.

11. The logger unit according to claim 10, wherein the logger unit is configured to be deactivated when it is removed from the absorbent article.

12. The logger unit according to claim 10, wherein the logger unit is configured to transmit the data recorded therein to a location remote of the logger unit.

13. A combination comprising the logger unit according to claim 10 and an absorbent article.

14. The combination according to claim 13, wherein the absorbent article comprises one or more sensor elements;
 wherein the logger unit is connectable to the one or more sensor elements; and
 wherein the processor of the logger unit is configured to acquire the absorption state of the absorbent article from the one or more sensor elements.

15. A method of processing data indicating an absorption state of an absorbent article, the method comprising
 receiving sets of data indicating the absorption state of the absorbent article, wherein each of the sets of data indicates the absorption state of the absorbent article over a portion of a continuous period of time; and
 displaying the sets of data in continuous form for the entire continuous period of time.

16. A method of processing data indicating an absorption state of an absorbent article, the method comprising
 receiving sets of data indicating the absorption state of the absorbent article, wherein each of the sets of data indicates the absorption state of the absorbent article over a portion of a continuous period of time; and
 collating the sets of data so as to obtain a single set of data indicating the absorption state of the absorbent article over the continuous period of time, wherein the single set of data includes portions of the continuous period of time in which no indication on the absorption state of the absorbent article is provided.

17. The method according to claim 16, further comprising displaying the single set of data in continuous form.

18. A data processing unit for processing data indicating an absorption state of an absorbent article, comprising:
 a processor configured to receive sets of data indicating the absorption state of the absorbent article, wherein each of the sets of data indicates the absorption state of the absorbent article over a portion of a continuous period of time; and
 a display configured to display the sets of data in continuous form for the entire continuous period of time.

19. The data processing unit according to claim 18, further comprising a display configured to display time intervals in the data in which no indication on the absorption state of the absorbent article is provided.

20. The data processing unit according to claim 18, further comprising a display configured to display the number of segments of the absorbent article which have absorbed liquid.

21. A data processing unit for processing data indicating an absorption state of an absorbent article, comprising a processor
 configured to receive sets of data indicating the absorption state of the absorbent article, wherein each of the sets of data indicates the absorption state of the absorbent article over a portion of a continuous period of time; and
 configured to collate the sets of data so as to obtain a single set of data indicating the absorption state of the absorbent article over the continuous period of time, wherein the single set of data includes portions of the continuous period of time in which no indication on the absorption state of the absorbent article is provided.

22. The data processing unit according to claim 21, further comprising a display configured to display the single set of data in continuous form.

* * * * *